(12) United States Patent
Comini

(10) Patent No.: US 11,793,898 B2
(45) Date of Patent: Oct. 24, 2023

(54) SANITATION ASSEMBLY AND METHOD

(71) Applicant: Merck Patent GmbH, Darmstadt (DE)

(72) Inventor: Fabrice Comini, Selestat (FR)

(73) Assignee: Merck Patent GmbH, Darmstadt (DE)

( * ) Notice: Subject to any disclaimer, the term of this patent is extended or adjusted under 35 U.S.C. 154(b) by 649 days.

(21) Appl. No.: 16/651,070

(22) PCT Filed: Sep. 24, 2018

(86) PCT No.: PCT/EP2018/075732
§ 371 (c)(1),
(2) Date: Mar. 26, 2020

(87) PCT Pub. No.: WO2019/063455
PCT Pub. Date: Apr. 4, 2019

(65) Prior Publication Data
US 2020/0222565 A1    Jul. 16, 2020

(30) Foreign Application Priority Data
Sep. 27, 2017  (EP) .................................... 17290125

(51) Int. Cl.
*A61L 2/18* (2006.01)
*A61L 2/24* (2006.01)
*A61L 2/26* (2006.01)

(52) U.S. Cl.
CPC .................... *A61L 2/18* (2013.01); *A61L 2/24* (2013.01); *A61L 2/26* (2013.01); *A61L 2202/121* (2013.01);
(Continued)

(58) Field of Classification Search
CPC ..... A61L 2/18; A61L 2/24; A61L 2/26; A61L 2202/121; A61L 2202/14; A61L 2202/17; A61L 2202/24
See application file for complete search history.

(56) References Cited

U.S. PATENT DOCUMENTS

| 5,526,841 A | 6/1996 | Detsch et al. |
| 8,808,621 B2 | 8/2014 | Akahori et al. |

(Continued)

FOREIGN PATENT DOCUMENTS

| CN | 204951932 U | 1/2016 |
| EP | 1195145 A1 | 4/2002 |

(Continued)

OTHER PUBLICATIONS

Office Action in corresponding JP application 2020-517504 dated Sep. 12, 2022 (pp. 1-2) and english translation thereof (pp. 1-2).

(Continued)

*Primary Examiner* — Sean E Conley
(74) *Attorney, Agent, or Firm* — MILLEN, WHITE, ZELANO & BRANIGAN, PC; Ryan Pool

(57) ABSTRACT

A sanitation assembly (1) comprising a first chamber (2) with a first volume (2a) for receiving a first fluid, and a second chamber (3) with a second volume (3a) for receiving a second fluid, wherein the first volume (2a) communicates with an outlet (6) of the assembly (1) via a first valve mechanism (4) configured to allow discharge of the fluid from the first volume (2a) to the outlet (6) at a predefined first opening pressure, wherein the second volume (3a) communicates with the outlet (6) of the assembly (1) via a second valve mechanism (5) configured to allow discharge of the fluid from the second volume (3a) to the outlet (6) at a predefined second opening pressure, and wherein the predefined second opening pressure of the second valve mechanism (5) is higher than the predefined first opening pressure of the first valve mechanism (4).

20 Claims, 2 Drawing Sheets

(52) U.S. Cl.
CPC ....... *A61L 2202/14* (2013.01); *A61L 2202/17* (2013.01); *A61L 2202/24* (2013.01)

(56) References Cited

U.S. PATENT DOCUMENTS

| | | |
|---|---|---|
| 8,808,622 B2 | 8/2014 | Arnold et al. |
| 9,180,217 B2 | 11/2015 | Arnold et al. |
| 2002/0033362 A1 | 3/2002 | Castellini |
| 2014/0158708 A1 | 6/2014 | Freudenberg et al. |

FOREIGN PATENT DOCUMENTS

| | | | | |
|---|---|---|---|---|
| EP | 1195145 B1 | 5/2006 | | |
| JP | 5253461 B2 | 7/2013 | | |
| WO | 2005067986 A1 | 7/2005 | | |
| WO | 2011083633 A1 | 7/2011 | | |
| WO | WO 2017/102621 A1 * | 6/2017 | ............ | A61M 5/168 |

OTHER PUBLICATIONS

International Search Report dated Nov. 28, 2018 issued in corresponding PCT/EP2018/075732 application (5 pages).
English Abstract of CN 204951932 U published Jan. 13, 2016.
Office Action in corresponding Vietnamese application 1-2020-02367 dated Jun. 27, 2023 (pp. 1-2) and english translation thereof (p. 1).

* cited by examiner

SANITATION ASSEMBLY AND METHOD

TECHNICAL FIELD

The invention concerns a sanitation assembly for use in decontamination, cleaning in place (CIP) or sanitizing in place (SIP) processes, especially in the pharmaceutical, biopharmaceutical, biotech, hospital, food and beverage industries but also in diagnostic, health care and research applications and a method of sanitizing a flowpath of a piece of equipment in these processes using a sanitation assembly.

Decontamination, cleaning or sanitation processes are regularly applied in the above industries to flow paths in pumps, pipes, tubes, valves or other pieces of equipment of systems that are subject to contamination. The processes typically involve a first stage where a disinfectant reagent is pumped through the respective equipment for a desired disinfect contact time, followed by a second stage where a rinsing fluid, often water, is pumped through the equipment to purge the equipment from the disinfectant reagent.

In this description the term "sanitizing" will be used to describe and cover all cleaning processes that are based on the sequential passing of at least two different fluids or reagents through a piece of equipment by means of a reduced suction pressure that is typically caused by a pumping action downstream of the point where the disinfectant reagent and rinsing fluid are introduced into the flowpath.

Existing processes involve either manual introduction of the disinfectant reagent and of the rinsing fluid in the necessary predetermined amounts and sequence including monitoring of the process or they require a complex and time consuming setup of dedicated hardware including sensors, valves, actuators, tubing, containers and programmed controllers for an automated process.

The invention has as its object to simplify the sanitation/cleaning process.

Means for Solving the Problem

The invention proposes a sanitation assembly with the features of claim 1 and a method of sanitizing a flowpath of a piece of equipment with the features of claim 14. Preferred embodiments are respectively defined in the dependent claims.

A sanitation assembly according to the invention comprises a first chamber with a first volume for receiving a first fluid, and a second chamber with a second volume for receiving a second fluid, wherein the first volume communicates with an outlet of the assembly via a first valve mechanism configured to allow discharge of the fluid from the first volume to the outlet at a predefined first opening pressure, wherein the second volume communicates with the outlet of the assembly via a second valve mechanism configured to allow discharge of the fluid from the second volume to the outlet at a predefined second opening pressure, and wherein the predefined second opening pressure of the second valve mechanism is higher than the predefined first opening pressure of the first valve mechanism.

The sanitation assembly of the invention provides a device, accessory or kit that can be simply and intuitively used to automatically sanitize (clean/disinfect) the flowpath of a piece of equipment, i.e. a pump, and that can be controlled only based on a timer or manually controlled sequential operation of the pump (the pump to be cleaned or another pump in communication with the flowpath to be cleaned) with two different pumping speeds or suction pressures within a sanitizing cycle, wherein the higher speed or pressure is activated after lapse of a predetermined period of contact time of the disinfectant with the flowpath to be cleaned.

Since the disinfectant reagent is kept in a separate volume from the rinsing fluid, a mixing of the disinfectant with the rinsing fluid can be avoided. Since the valve mechanisms allow discharge of the respective fluids at different pressure levels and the valve mechanism of the rinsing fluid allows discharge at the higher level, the disinfectant reagent is completely empty before the reagent rinsing is started. Since the sanitation assembly is closed, any contamination of the fluid flowpath to be cleaned is avoided during the sanitation cycle. Since the valve mechanisms allow discharge of the respective fluids open automatically (i.e. open automatically in case valves, preferably check valves are used) when the "cracking pressure" is reached at the downstream side of the respective valve mechanism (or prevent discharge or close when the pressure falls below that value), no external sensors, valves or actuators are required to set up the sanitizing process and no further manual user handling is required except for the initial connection of the one-piece assembly to the flowpath and an initiation of the pump operation sequence.

Preferably, the first volume does not communicate with a vent. Thus, if the pump is stopped during the contact time, the fluid (i.e. the disinfectant reagent) stays in the volume and pump tubes without draining by gravity and leaking through the flowpath or pump. In this case the retaining of the fluid in the volume can serve as the first valve mechanism that allows discharge of the fluid only after a certain defined minimum pressure differential is applied on the first volume that is lower than that with respect to the second opening pressure. A typical example of a suitable structure is where the first volume is implemented by a syringe that is preferably removably attached to a connector communicating with the outlet.

Preferably, at least the first chamber is configured such that the size of the first volume is reduced when the first fluid is discharged from the first volume. This is the case also where the syringe is used.

Preferably, the first chamber comprises a collapsible bag.

Preferably, the first chamber comprises a rigid cylinder and a piston movably received in the cylinder. This is the case also where the syringe is used.

Preferably, the second volume communicates with a vent.

Preferably, the first chamber comprises a rigid cylinder and has a hydrophilic membrane at a fluid outlet from the first volume.

Preferably, the second chamber comprises a collapsible bag or a rigid container.

Preferably, the first and second volumes are received in a common, preferably rigid housing.

Preferably, the first and the second volumes are concentric.

Preferably, the outlet of the assembly is configured to be connected to a head of a vacuum pump or vacuum bar.

Preferably, the first and second valve mechanisms are normally closed valves, preferably check valves that are configured to open at a sub-ambient pressure existing at the outlet side of the respective valves.

Preferably, the sanitation assembly further comprises a disinfectant reagent contained in the first volume of the first chamber as the first fluid and preferably a rinsing fluid, preferably water, contained in the second volume of the second chamber as the second fluid.

The invention also concerns a method of sanitizing a flowpath of a piece of equipment, comprising preparing a sanitation assembly according to the invention and connecting the outlet of the assembly with an upstream side of a vacuum pump or vacuum bar, operating the vacuum pump or vacuum bar with a first speed or pressure for a predetermined period of time to open the first valve mechanism and empty the disinfectant reagent from the first volume, stopping the vacuum pump or vacuum bar for a predetermined period of contact time of the disinfectant with the flowpath to be sanitized, and operating the vacuum pump or vacuum bar with a second speed or pressure for a predetermined period of time to open the second valve mechanism and empty the rinsing fluid from the second volume, wherein the second speed is higher than the first speed or the second pressure is lower than the first pressure.

In a preferred variation of the method the first volume is replaced by a pressure gauge and the pressure is measured while emptying the rinsing fluid from the second volume. This variant allows a user to measure the pressure for emptying the second volume. At the same time the user may measure the time required for emptying the second volume in order to determine the flow rate of the vacuum pump or vacuum bar. The flow rate and pressure measurement allow the user to simply verify the correct operation and function of the vacuum pump or vacuum bar.

BRIEF DESCRIPTION OF DRAWINGS

Preferred embodiments of the sanitation assembly according to the present invention will be described by reference to the attached drawings, in which.

DETAILED DESCRIPTION OF THE EMBODIMENTS

Figure 1:
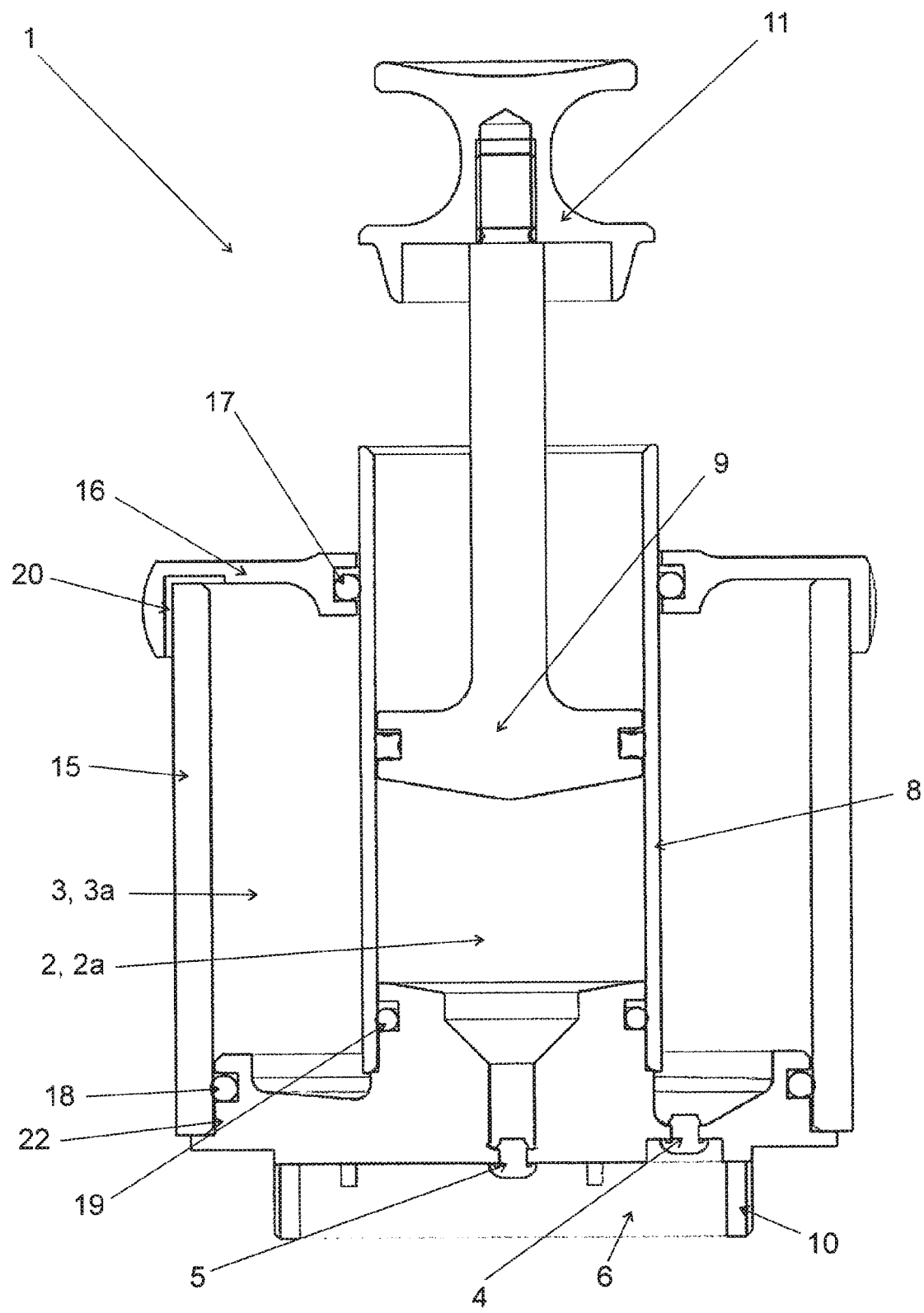
FIG. 1 is a schematic concept diagram for illustrating the working principle of a sanitation assembly according to a first embodiment of the invention.

A sanitation assembly 1 according to the invention generally comprises a first chamber 2 which defines a first volume 2a for receiving a first fluid (preferably the disinfectant or sanitation reagent) and a second chamber 3 which defines a second volume 3a for receiving a second fluid (preferably a rinsing fluid like water). The first volume 2a communicates with an outlet 6 of the assembly 1 via first valve mechanism 4 configured to allow discharge of the fluid from the first volume 2a to the outlet 6 of the assembly 1 at a predefined first opening pressure (i.e. a normally closed first valve 4 configured to open at a predefined opening pressure for discharging the fluid from the first volume 2a to the outlet 6 as shown in FIG. 1), and the second volume 3a communicates with the outlet 6 of the assembly 1 via a second valve mechanism 5 configured to allow discharge of the fluid from the second volume 3a to the outlet 6 at a predefined second opening pressure (i.e. a normally closed second valve 5 configured to open at a predefined opening pressure for discharging the fluid from the second volume 3a to the outlet 6 of the assembly 1 as shown in FIG. 1). The predefined opening pressures of the valve mechanisms are sub-ambient or negative pressures existing at the outlet side of the respective valve or volume and the predefined opening pressure of the second valve mechanism 5 is higher (i.e. more reduced) than that of the first valve mechanism 4. In other words, in the first embodiment shown in FIG. 1 the valve mechanisms are valves, preferably in the form of normally closed check valves that open automatically when the respective "cracking pressure" is reached at the downstream side of the respective valve and the "cracking pressures" of the two valve mechanisms (i.e. of the valves) from which the discharge of the fluids from the respective volumes is possible are different from each other. The opening pressure of the first and second valve mechanisms are preferably set such that the first volume is be completely empty before the second valve mechanism opens.

The first volume 2a defined by the first chamber 2 does not communicate with a vent and the first chamber 2 is configured such that the size of the first volume 2a is reduced when and as the first fluid is discharged from the first volume 2a. This can be realized in that the first chamber 2 is similar to a conventional syringe 12 as exemplified by the second embodiment shown in FIG. 2 and described below, with the difference to the first embodiment that the syringe does not necessarily require a valve, in particular a check valve to prevent discharge of the fluid from the volume below a predetermined pressure existing at the outlet. The term "valve mechanism" as used in this specification accordingly is to encompass not only dedicated valve arrangements that open below a certain predetermined pressure differential but also a structure where the fluid in the volume is prevented from flowing out into the outlet below a certain predetermined pressure differential due to the fact that no vent is provided to communicate with the volume.

Figure 2:
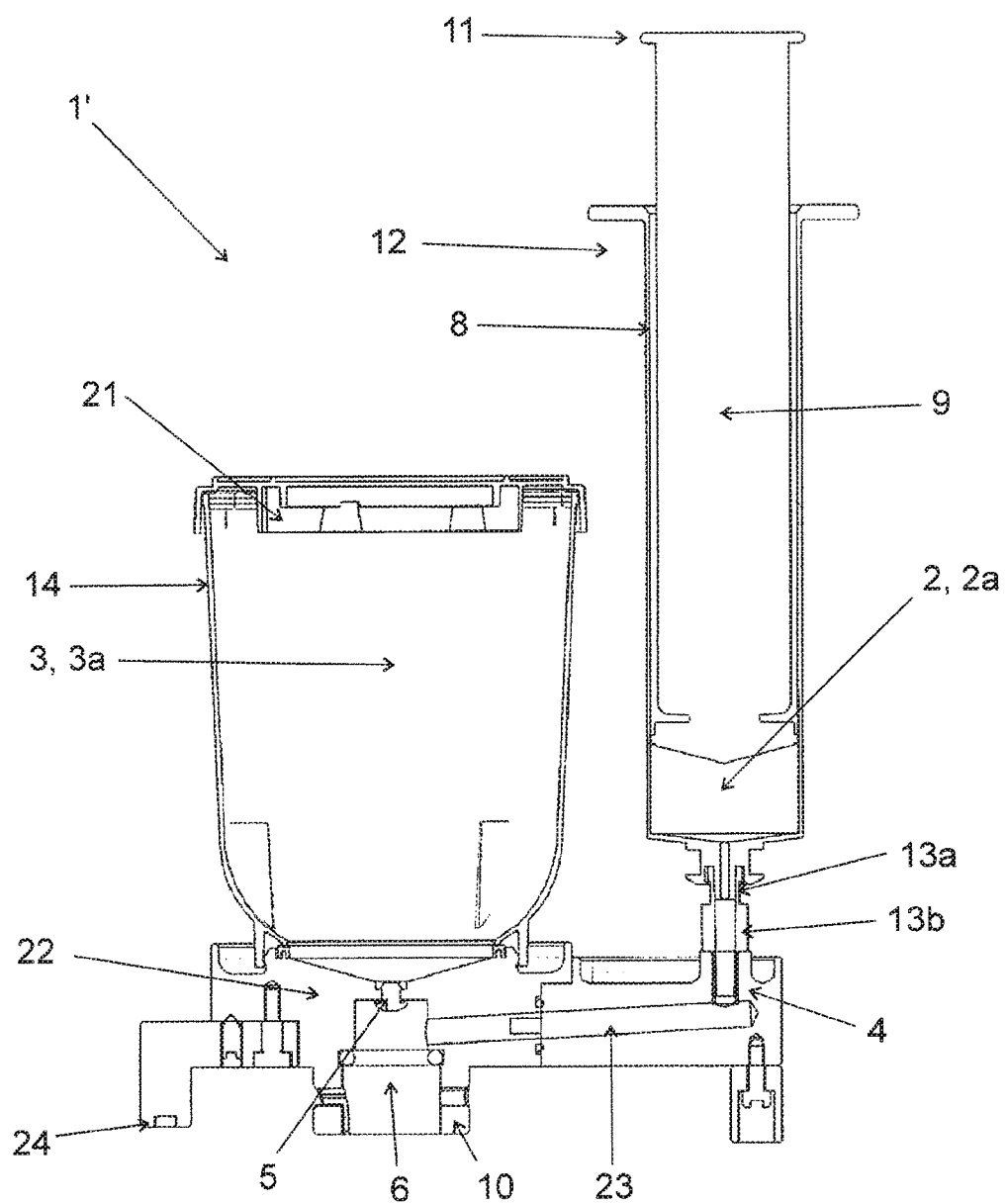
FIG. 2 is a schematic concept diagram for illustrating the working principle of a sanitation assembly according to a second embodiment of the invention.

The first chamber 2 may be formed as a rigid cylinder and may be provided with a hydrophilic membrane (not shown) at a fluid outlet from the first volume 2a. This will also close the chamber when the fluid is completely empty and prevent that air is sucked to allow the second chamber 3 to open. The hydrophilic membrane may be integrated in the first chamber 2 or in the base 22 of the assembly (to be described later). The first chamber 2 of the sanitation assembly of both embodiments comprises a rigid cylinder or barrel 8 and a piston or plunger 9 movably received in the cylinder 8 and closing an end opening of the cylinder (as shown in FIGS. 1 and 2) or the first chamber 2 may alternatively comprise a collapsible flexible bag (not shown). The reduced pressure existing at the outlet of the first volume 2a will thus pull the piston 9 towards the outlet (or valve if provided) or will collapse the volume of the bag while it is being emptied.

The second volume 3a can communicate with a vent 20 or can have an opening. The second chamber 3 may alternatively also be a collapsible, flexible bag.

The use of collapsible bags for the first and second chambers is preferred as it allows the use of pre-packaged and sealed pre-sterilized fluids for both the disinfectant reagent and the rinsing fluid and it reduces the amount of waste. The use of a flexible, collapsible bag for one or both fluids can be combined with a preferably rigid housing in which the first and second volumes 2a,3a are received (not shown).

In a variant of the first and second embodiments the first chamber can be in the form of a (standard) disposable syringe 12 that is preferably removably received in a rigid housing or, as shown in FIG. 2, is removably connected to a syringe connector 13a provided on a base 22 of the assembly 1' with its outlet adapter 13b. The syringe connector 13a may in this case be configured to receive a luer lock tip, a slip tip or a tapered tip of a outlet adapter of the syringe 12. In this case the second chamber can be formed as an integral section of the housing or can be in the form of a flexible collapsible bag received in the housing. Of course, both chambers can be formed as integral sections of a common housing and, independent from the structure chosen, the first and the second volumes 2a,3a can be concentrically arranged so that the normally smaller first volume (for accommodating the disinfectant reagent) is in the center and the normally larger second volume (for accommodating the rinsing fluid), is arranged at the periphery of the first volume (see FIG. 1).

The sanitation assembly 1 as shown in FIG. 1 for example has the base 22 provided with seals 18, 19 defining, together with concentric rigid cylinders 8 and 15 the first and second chambers 2, 3. The second chamber 3 is provided with a removable cover 16 that can be provided with a further seal 17 that seals against the (inner) cylinder 8. The vent 20 is defined as a predefined opening between the upper edge of the (outer) cylinder 15 and the cover 16. Although not necessarily required the plunger or piston 9 of the first chamber is provided with a handle or grip 11 at the upper end to facilitate withdrawing of the plunger.

The downstream sides of the first and second valves 4, 5 (or of the first and second volumes if no valves are provided as described above) communicate with the common outlet 6 of the assembly 1, 1' and the outlet 6 is preferably configured to be connected to a head 7 of a vacuum pump or vacuum bar in that the base 22 is provided with a suitable mating outlet connector 10. Use of adapters is possible to adapt the assembly to different types of vacuum pumps or vacuum bars.

The sanitation assembly 1' according to the second embodiment shown in FIG. 2 differs from the assembly 1 according to the first embodiment shown in FIG. 1 in that the first volume 2a is formed by a standard disposable syringe 12 removably attached to a syringe connector 13b formed on the base 22 in a vertical tip-side down orientation. The syringe connector 13b communicates with the outlet 6 through an internal passage 23 since the second volume 3a is formed by a separate rigid funnel-like container 14 provided with a lid or cover 21 and arranged adjacent to the syringe. The outlet of the funnel-like container 14 at its bottom end or the receptacle for the container 14 in the base 22 is provided with a valve 5 as described above that also communicates with the outlet 6.

The sanitation assembly 1, 1' according to the invention can be prepared as a kit or accessory that has the disinfectant reagent contained in the first volume 2a of the first chamber 2 as the first fluid and the rinsing fluid, preferably water, contained in the second volume 3a of the second chamber 3 as the second fluid. The second volume can, however, be empty in the manufactured state and can be provided with an opening or a removable lid or cover through a user may fill-in a desired purging fluid. The first container, for example in the form of the syringe, and/or the second container may be separated from the base in the initial state or provided separately as disposable replacements while the base can be multi-usable. Arranging the syringe adjacent to the second container on the base facilitates its removal from the base and the use of standard components. While the sanitation assembly of the invention is mainly described in connection with the use for sanitizing a pump itself, the sanitizing assembly can be generally applied to cleaning processes that are based on the sequential passing of at least two different fluids or reagents through a flowpath of a piece of equipment by means of a reduced suction pressure that is typically caused by a pumping action downstream of the point where the at least two fluids (for example disinfectant reagent and rinsing fluid) are introduced into the flowpath.

In a variation of the method the first volume, especially if in the form of the syringe removably attached to the base as in the second embodiment, can be replaced by a pressure gauge that fits into the same connector and by means of which the pressure can be measured while emptying the rinsing fluid from the second volume. This variant allows a user to measure the pressure (visually or electronically) for emptying the second volume. At the same time the user may measure the time required for emptying the second volume in order to determine the flow rate of the vacuum pump or vacuum bar. The flow rate and pressure measurement allow the user to simply verify the correct operation and function of the vacuum pump or vacuum bar that is being sanitized.

In this example a magnet 24 can be provided on a movable lever or holder to cooperate with a sensor to enable or disable the sanitization sequence for sanitizing and testing the pump.

REFERENCE SIGNS 1 sanitation assembly
2 first chamber
2a first volume
3 second chamber
3a second volume
4 first valve mechanism
5 second valve mechanism
6 outlet
7 pump head
8 cylinder
9 piston
10 outlet connector
11 handle/grip
12 syringe (first chamber)
13a syringe adaptor
13b syringe connector
14 funnel (second chamber)
15 cylinder
16 cover
17 seal
18 seal
19 seal
20 vent
21 lid (cover)
22 base
23 passage
24 magnet

The invention claimed is:
1. A sanitation assembly (1;1') comprising:
a first chamber (2) with a first volume (2a) for receiving a first fluid, and
a second chamber (3) with a second volume (3a) for receiving a second fluid,
wherein the first volume (2a) communicates with an outlet (6) of the assembly (1) via a first valve (4) configured to allow discharge of the fluid from the first volume (2a) to the outlet (6) at a predefined first opening pressure,
wherein the second volume (3a) communicates with the outlet (6) of the assembly (1) via a second valve (5) configured to allow discharge of the fluid from the second volume (3a) to the outlet (6) at a predefined second opening pressure,
wherein the predefined second opening pressure of the second valve (5) is higher than the predefined first opening pressure of the first valve (4), and wherein the first valve (4) only dispenses the fluid of the first volume 2a, while the second valve (5) only dispenses the fluid of the second volume (3a).

2. The sanitation assembly (1;1') according to claim 1, wherein the first volume (2a) does not communicate with a vent and/or the second volume (3a) communicates with a vent (20).

3. The sanitation assembly (1;1') according to claim 1, wherein at least the first chamber (2) is configured such that the size of the first volume (2a) is reduced when the first fluid is discharged from the first volume (2a).

4. The sanitation assembly (1;1') according to claim 3, wherein the first chamber (2) comprises a collapsible bag.

5. The sanitation assembly (1;1') according to claim 3, wherein the first chamber (2) comprises a rigid cylinder (8) and a piston (9) movably received in the cylinder (8).

6. The sanitation assembly (1;1') according to claim 1, wherein the first chamber (2) comprises a rigid cylinder and has a hydrophilic membrane at a fluid outlet from the first volume (2a).

7. The sanitation assembly (1;1') according to claim 1, wherein the second chamber (3) comprises a collapsible bag or a rigid container (14).

8. The sanitation assembly (1) according to claim 1, wherein the first and second volumes (2a,3a) are received in a common housing.

9. The sanitation assembly (1) according to claim 1, wherein the first and the second volumes (2a,3a) are concentric.

10. The sanitation assembly (1;1') according to claim 1, wherein the outlet (6) of the assembly (1) is configured to be connected to a head (7) of a vacuum pump or vacuum bar.

11. The sanitation assembly (1) according to claim 1, wherein the first and second valves (4,5) are normally closed valves, that are configured to open at a sub-ambient pressure existing at the outlet side of the respective valves (4,5).

12. The sanitation assembly (1') according to claim 1, wherein at least the first valve is formed by the first volume (2a) of the first chamber (2) being not provided with a vent and allowing discharge of the fluid at the predefined first opening pressure that is higher than ambient pressure but lower than the second opening pressure.

13. The sanitation assembly (1;1') according to claim 1, further comprising:
a disinfectant reagent contained in the first volume (2a) of the first chamber (2) as the first fluid and a rinsing fluid, contained in the second volume (3a) of the second chamber (3) as the second fluid.

14. A method of sanitizing a flowpath of a piece of equipment, comprising:
preparing a sanitation assembly (1;1') according to claim 13 and connecting the outlet (6) of the assembly with an upstream side of a vacuum pump or vacuum bar;
operating the vacuum pump or vacuum bar with a first speed or pressure for a predetermined period of time to open the first valve (4) and empty the disinfectant reagent from the first volume (2a);
stopping the vacuum pump or vacuum bar for a predetermined period of contact time of the disinfectant with the flowpath to be sanitized; and
operating the vacuum pump or vacuum bar with a second speed or pressure for a predetermined period of time to open the second valve (5) and empty the rinsing fluid from the second volume (3a),
wherein the second speed is higher than the first speed or the second pressure is lower than the first pressure.

15. The method of sanitizing the flowpath of a piece of equipment according to claim 14, further comprising:
replacing the first volume (2a) by a pressure gauge and measuring the pressure while emptying the rinsing fluid from the second volume (3a).

16. The sanitation assembly of claim 5 additionally comprising, a syringe (12) which is removably attached to a connector (13) communicating with the outlet (6).

17. The sanitation assembly of claim 8, wherein the housing is ridged.

18. The sanitation assembly of claim 11, wherein the first and second valves are check valves.

19. A sanitation assembly (1;1') comprising:
a first chamber (2) with a first volume (2a) for receiving a first fluid, and
a second chamber (3) with a second volume (3a) for receiving a second fluid,
wherein the first volume (2a) communicates with an outlet (6) of the assembly (1) via a first valve (4) configured to allow discharge of the fluid from the first volume (2a) to the outlet (6) at a predefined first opening pressure,
wherein the second volume (3a) communicates with the outlet (6) of the assembly (1) via a second valve (5) configured to allow discharge of the fluid from the second volume (3a) to the outlet (6) at a predefined second opening pressure, and
further comprising a disinfectant reagent contained in the first volume (2a) of the first chamber (2) as the first fluid and a rinsing fluid contained in the second volume (3a) of the second chamber (3) as the second fluid.

20. A sanitation assembly (1;1') comprising:
a first chamber (2) with a first volume (2a) for receiving a first fluid, and
a second chamber (3) with a second volume (3a) for receiving a second fluid,
wherein the first volume (2a) communicates with an outlet (6) of the assembly (1) via a first valve (4) configured to allow discharge of the fluid from the first volume (2a) to the outlet (6) at a predefined first opening pressure,
wherein the second volume (3a) communicates with the outlet (6) of the assembly (1) via a second valve (5) configured to allow discharge of the fluid from the second volume (3a) to the outlet (6) at a predefined second opening pressure,
wherein the predefined second opening pressure of the second valve (5) is higher than the predefined first opening pressure of the first valve (4),
wherein at least the first chamber (2) is configured such that the size of the first volume (2a) is reduced when the first fluid is discharged from the first volume (2a), and
wherein the first chamber (2) comprises a rigid cylinder (8) and a piston (9) movably received in the cylinder (8).

* * * * *